(12) United States Patent
Charlez et al.

(10) Patent No.: US 10,182,747 B2
(45) Date of Patent: Jan. 22, 2019

(54) URINE MEASURING DEVICE

(75) Inventors: Mikael Charlez, Mölndal (SE); Mikael Löfgren, Mölndal (SE)

(73) Assignee: Observe Medical ApS, Kongens Lyngby (DK)

( * ) Notice: Subject to any disclaimer, the term of this patent is extended or adjusted under 35 U.S.C. 154(b) by 911 days.

(21) Appl. No.: 13/377,641

(22) PCT Filed: Jun. 23, 2010

(86) PCT No.: PCT/EP2010/058924
§ 371 (c)(1),
(2), (4) Date: Dec. 12, 2011

(87) PCT Pub. No.: WO2010/149708
PCT Pub. Date: Dec. 29, 2010

(65) Prior Publication Data
US 2012/0109008 A1    May 3, 2012

(30) Foreign Application Priority Data
Jun. 23, 2009 (SE) ........................... 0950482

(51) Int. Cl.
*A61B 5/145* (2006.01)
*A61B 5/20* (2006.01)

(52) U.S. Cl.
CPC .......... *A61B 5/14507* (2013.01); *A61B 5/208* (2013.01)

(58) Field of Classification Search
CPC ........................................................ A61B 5/00
USPC ................. 600/573, 574, 575, 578; 604/329
See application file for complete search history.

(56) References Cited

U.S. PATENT DOCUMENTS

| | | | | |
|---|---|---|---|---|
| 3,754,220 A | * | 8/1973 | Sztamler et al. | 340/609 |
| 3,912,455 A | * | 10/1975 | Lichtenstein | 422/430 |
| 3,919,455 A | * | 11/1975 | Sigdell et al. | 73/226 |
| 4,051,431 A | * | 9/1977 | Wurster | 73/861 |
| 4,137,940 A | * | 2/1979 | Faisandier | 137/486 |
| 4,237,878 A | * | 12/1980 | Kobayashi et al. | 604/122 |

(Continued)

FOREIGN PATENT DOCUMENTS

| | | |
|---|---|---|
| CN | 1340151 | 3/2002 |
| CN | 2856944 | 1/2007 |

(Continued)

OTHER PUBLICATIONS

International Search Report from corresponding International Application No. PCT/EP2010/058924.

(Continued)

*Primary Examiner* — May A Abouelela
(74) *Attorney, Agent, or Firm* — RMCK Law Group, PLC (57) ABSTRACT

A device for measuring of urine production of a patient carrying a urine catheter, the device comprising a replaceable self-emptying chamber (120), provided with a siphon for self emptying when the burette becomes filled up to a predetermined volume, the self-emptying chamber further comprises an inlet and an outlet for the urine whose volume is to be measured, further, the device comprises a base unit (105) provided with attachment organs for removably attaching the self-emptying chamber (120) to the base unit, which station having measurement organs for sensing the level of urine in the self-emptying chamber and for keeping track of number of self-emptyings.

27 Claims, 8 Drawing Sheets

(56) References Cited

U.S. PATENT DOCUMENTS

| | | | | |
|---|---|---|---|---|
| 4,432,761 | A | * | 2/1984 | Dawe .................... 604/253 |
| 4,448,207 | A | * | 5/1984 | Parrish .................... 600/584 |
| 4,554,687 | A | * | 11/1985 | Carter et al. .................... 4/144.2 |
| 4,562,936 | A | * | 1/1986 | Deflander .................... 220/268 |
| 4,683,748 | A | * | 8/1987 | Carter .................... 73/226 |
| 5,062,304 | A | * | 11/1991 | Van Buskirk et al. ......... 73/861 |
| 5,125,265 | A | * | 6/1992 | O'Connell et al. .......... 73/61.41 |
| 5,135,485 | A | * | 8/1992 | Cohen et al. .................... 604/67 |
| 5,263,370 | A | * | 11/1993 | Murata et al. .................... 73/226 |
| 5,483,830 | A | * | 1/1996 | Dietz et al. .................... 73/226 |
| 5,807,278 | A | * | 9/1998 | McRae .................... 600/579 |
| 5,891,051 | A | * | 4/1999 | Han et al. .................... 600/573 |
| 6,491,659 | B1 | * | 12/2002 | Miyamoto .................... 604/30 |
| 6,562,012 | B1 | * | 5/2003 | Brown et al. .................... 604/253 |
| 6,640,649 | B1 | * | 11/2003 | Paz .................... A61M 5/1689 73/861.41 |
| 7,107,837 | B2 | * | 9/2006 | Lauman .............. A61M 1/1658 73/232 |
| 7,416,542 | B2 | * | 8/2008 | Aundal .................... 604/317 |
| 7,722,584 | B2 | * | 5/2010 | Tanaka et al. .................... 604/317 |
| 7,798,586 | B2 | * | 9/2010 | Watanabe .................... 347/7 |
| 2002/0053104 | A1 | * | 5/2002 | Rump .................... E03D 5/105 4/313 |
| 2002/0055725 | A1 | * | 5/2002 | Verkaart et al. .............. 604/319 |
| 2003/0144646 | A1 | * | 7/2003 | Se et al. .................... 604/409 |
| 2005/0247126 | A1 | * | 11/2005 | Eguchi et al. .............. 73/304 R |
| 2006/0270971 | A1 | * | 11/2006 | Gelfand et al. .................. 604/66 |
| 2008/0004576 | A1 | * | 1/2008 | Tanaka et al. ................. 604/317 |
| 2009/0040262 | A1 | * | 2/2009 | Watanabe ........................ 347/19 |
| 2009/0287170 | A1 | * | 11/2009 | Otto ............................ 604/318 |
| 2009/0314101 | A1 | * | 12/2009 | Levine ....................... 73/861.08 |
| 2010/0211032 | A1 | * | 8/2010 | Tsai et al. ..................... 604/319 |

FOREIGN PATENT DOCUMENTS

| | | |
|---|---|---|
| JP | 49-075171 S | 7/1974 |
| JP | 58-130026 S | 8/1983 |
| JP | 06-504698 H | 6/1994 |
| JP | 10-509056 H | 9/1998 |
| JP | 2002-535607 | 10/2002 |
| WO | 9505774 | 3/1995 |
| WO | 0042394 | 7/2000 |
| WO | 0160255 | 8/2001 |
| WO | 0182772 | 11/2001 |
| WO | 2007079942 | 7/2007 |
| WO | 2007148892 | 12/2007 |
| WO | 2008129640 | 10/2008 |
| WO | 2009052496 | 4/2009 |

OTHER PUBLICATIONS

Translation of Search Report from Corresponding Japanese Patent Application No. 2012-516721, dated May 26, 2014.

* cited by examiner

SECTION C-C
Fig.4d

Fig.4e

SECTION B-B
Fig.4f

SECTION E-E
Fig.4g

Fig.6

URINE MEASURING DEVICE

TECHNICAL FIELD

The present invention relates to a device and a method for measuring the urine production of a patient. In particular the present invention relates to a device for measuring the amount of urine volume passing from a catheter inserted in the urine bladder of a patient and further passing through a self emptying measuring chamber of the device and further being collected in a collection bag.

BACKGROUND ART

A simple known method of measuring urine production is to collect the produced urine via a catheter in a bag. A nurse replaces the bag with an empty bag at regular time intervals and notes the time and the volume produced since last replacement, and calculates manually a figure representing urine production. Such a method is relatively slow, labour intensive, and inaccurate as to variations in urine production volume during the interval between replacements of the collection bag.

Attempts have been made to improve measurements;

U.S. Pat. No. 3,919,455 describes a device comprising a siphon chamber for the urine with a self emptying function, and wherein the urine volume is measured with the aid of an optic and/or electric sensor. When the urine level in the siphon chamber increases, the capacitance between two electrodes in the walls of the siphon chamber changes. In this way a signal is created that corresponds to the amount of urine in the siphon chamber. See e.g. FIG. 4 and column 4 lines 34 to 52.

GB2243918 describes a siphoning sensor in contact with fluid.

A problem of prior art is how to accomplish real time measurements. Another problem is how to provide intelligent programmed system loops that identifies prolonged emptying procedure. Some systems that offer volume calculation were either in direct contact with the fluid or comprise an optic sensor or a scale that provides the information over time.

SUMMARY OF THE INVENTION

The present invention overcomes the problems of prior art by providing a measurement device comprising a replaceable vessel, preferably a siphoning chamber, also called a "burette", that is to be placed in removable close proximity to electrodes arranged on a surface of a base unit. Said base unit may also comprise measurement electronics. It is an advantage to arrange as much of measurement electronics in the base unit to make the replaceable burette able to manufacture at low cost. The electrodes on the surface of the base unit provides for contactless capacitive measurement of urine level in the burette. The base unit may also comprise electrodes for making contact with electrodes that are provided in the burette to make conductance measurements on the urine therein. It is an advantage to monitor the conductivity of the urine to be able to estimate the concentration of ions therein, which may give the responsible physician valuable information on kidney function. Conductance measurements may also improve urine volume measurements as will be explained below. The burette may be produced in a transparent polymer material to allow for visibility and for good signal conditions.

In this way is provided a liquid volume sensing apparatus which can be used for measuring the volume of urinary output in real time, hourly and accumulated during the course of treatment. The invention may rely on tubing to be connected to a patient's urinary catheter, and comprise a vented siphoning burette, a one way valve, a reservoir and a controller (base) unit. The burette has a volume and in combination with the one way valve it prevents bacteria from going upstream and reaching the patient, which bacteria could otherwise cause a urinary tract infection (UTI).

The device may measure the urinary output in real time, hourly and accumulated for at least 24 hours. Monitoring of the hourly urinary production through the burette is measured by a suitable sensor system that does not need to be in direct contact with the urine, e.g. as described above. The base unit may have a cavern for placing the burette, and the walls of the cavern may be provided with two or more electrodes for measuring the capacitance between them. As the level of urine in the burette changes, the capacitance changes and may provide a measure corresponding to the level of urine. The electrodes may comprise a conductive film/sheet/tape/foil that functions as a capacitive element that detects fluid volume through the wall of the burette. Suitably the wall of the burette is not thicker that 2.0 mm to allow for good measuring conditions. The change of capacitance of the capacitive elements is measured and this is translated to a volume stored as a digital value by a microcontroller or similar processing unit, suitably contained in the base unit. Using a single chip microcontroller optimises performance and power consumption.

The timing and the intervals of emptying procedure may be monitored and analysed by the microprocessor in order to detect real time values, hourly volume and to keep track on accumulated values. The inside of the burette could preferably be coated with a hydrophobic coating and the outlet of the burette into the collection bag could have a wide angled design. This combination speeds up the emptying mechanism and prevents fluid from being pooled in the burette system. The base unit may be provided with a communications unit for wireless communication to a remote unit for increasing the surveillance and usability of the system during surgical and intensive care procedures. The communication may use radio waves, or infrared technique. It may be a great advantage for personnel during surgery to be able to monitor urine production without needing to lean or bend deep down forward to read urine production from a graduation of a collection bag or the like.

The present invention is an improvement of the prior art though it overcomes the related problems during urinary output monitoring procedure by providing a totally automatic minimal battery powered device for calculating, measuring, storing and displaying the said procedure. In addition to this it provides an immediate value of the current volume, providing a faster and more direct response to both volume and rate than prior art.

The device also overcomes the related problems from accuracy and subjectivity during the said procedure. The device may comprise a capacitive sensor system that does not need to stand in immediate contact with the urine.

The device may also comprise a pre-alarm setting that allows the user to set a certain urinary output tolerance in what is acceptable or not, and there may also be provided an alarm mode that alerts the user to check patients urinary output in case of any alarm event.

The system may also offer an event marker that synchronises the therapy given to the patient in correlation to the urinary output.

The alarm system may also provide wireless means capable to send urinary output information and/or an alarm direct to a patient monitoring device that easily can be located in the same room as the responsible personnel. Furthermore the urine measuring device or the patient monitoring device, or both, may be provided with means, such as connections, interfaces and/or slots, to transfer urine measurements information, e.g. urine production curve(s), and/or urine conductivity curves to memory devices such as USB (Universal Serial Bus)-memory sticks or SD (Secure Digital) memory cards.

The present invention provides for a prevention of dehydration or overload during a medical procedure and the wireless alarm capability improves safety during the procedure in relation to known technology.

Thus, according to a first aspect of the invention there is provided a urine measuring device for measuring of urine production of a patient carrying a urine catheter, comprising a self-emptying chamber, which in turn comprises an inlet connectable to the catheter and an outlet for the urine whose volume is to be measured, the device further comprises a base unit having an attachment organ for removably attaching the self-emptying chamber to the base unit, the base unit also being provided with a urine level measurement organ, capable of sensing changes in the level of urine in the self-emptying chamber, thereby producing a urine level signal. The base unit further comprises a processor arranged to calculate the volume of urine produced based on the urine level signal measured by the urine level measurement organ.

The processor is arranged to detect, based on the urine level signal, self emptyings. And further to keep record of how many times the self-emptying chamber has been emptied. The processor is thus arranged to calculate the urine production as a function of time.

The device may comprise two or four capacitance electrodes placed apart relative to each other such that when the self-emptying chamber is attached to the base unit, the capacitance electrodes are capable of sensing a capacitance signal occurring between the two capacitance electrodes, which capacitance signal changes as the level of urine in the self-emptying chamber changes, and the capacitance signal therefore constitutes a measure of the produced amount of urine.

The self-emptying chamber may be a disposable article.

The organs for removably attaching the self-emptying chamber to the base unit may be an open cavern, or a fenestrated open cavern. The cavern may be defined by a first limiting entity, a second limiting entity, and a third limiting entity. The limiting entities may be walls.

The urine level measurement organ may comprise an ultrasound meter system for determining the level of urine in the self-emptying chamber.

The ultrasound meter system may comprise an ultrasound transducer arranged at the base unit for emitting and receiving ultrasound. The self-emptying chamber may be provided with an ultrasound beam reflector for directing an ultrasound beam towards the urine fluid surface. The self-emptying chamber may be provided with a hydrophobic filter arranged to let an ultrasound beam pass from the ultrasound transducer through an opening in the wall of the self-emptying chamber provided with the hydrophobic filter, and into the interior of the self-emptying chamber.

The urine level measurement organ comprises a pressure metering system for determining the level of urine in the self-emptying chamber. The pressure metering system may comprise an ascending pipe having organs to be removably connectable to a pressure sensor of the base unit.

The self-emptying chamber may have a measurement volume of between 10 and 30 milliliter. The self-emptying chamber may have a measurement volume of between 14 and 16 milliliter.

The self-emptying chamber may have a quadratic or oval cross section and be provided with at least one planar wall to fit snugly toward the capacitance electrodes.

A front wall of the self-emptying chamber may be made of a transparent material, suitably a polymer.

The device may have two conductance electrodes arranged on the inside of the self-emptying chamber to come into contact with the urine and also being connected to contact plates arranged on the outside of the self-emptying chamber. The contact plates arranged on the outside of the self-emptying chamber may be arranged at a back wall of the self-emptying chamber. Two connection contacts may be arranged in a back wall of the cavern of the base unit to make contact to the contact plates of the self-emptying chamber to convey a conductance signal to the base unit for signal processing and measurements. The processor may be arranged to calculate the volume of urine produced based on capacitance measurements and conductance measurements in combination. The processor may be arranged to calculate the volume of urine produced based on capacitance and ultrasound measurements in combination. The device may be provided with a urine conductivity meter and the processor may be arranged to calculate the volume of urine produced based on capacitance, ultrasound, and conductivity measurements in combination.

The device may be provided with an outlet pipe of a certain length and wherein a cross section area is gradually increasing towards an outlet end of the outlet pipe.

The device may be provided with an input organ for marking a point in time. The point in time may be the time of administering a drug. The marking may be a push of a button and the processor may be arranged to store the current time.

According to a second aspect is provided a self-emptying chamber as described above.

According to a third aspect is provided a self-emptying chamber for use in a device as described above.

According to a fourth aspect is provided a self-emptying chamber for use together with a base unit as described above.

According to a fifth aspect there is provided a base unit as described above.

According to a sixth aspect there is provided a base unit for use in a urine measuring device as described above.

According to a seventh aspect there is provided a base unit for use together with a self emptying chamber as described above.

According to an eighth aspect there is provided a method for monitoring the urine production comprising the following steps:

letting urine pass into a replaceable self emptying vessel;
measuring continuously the urine level in the vessel using electronic level measuring organs arranged apart from the self emptying vessel;
detecting self emptying events of the self emptying vessel;
keeping track of urine production as a function of time based on the urine level measurement and detection of self emptying events;

The method may also comprise the steps of:
displaying urine production on an electronic display;
communicating urine production information to a remote unit.

BRIEF DESCRIPTION OF THE DRAWINGS

The invention will now be further explained with the aid of one or more embodiments of the invention in conjunction with the accompanying drawings of which:

FIGS. 1c and 1d shows in more detail a base unit part of the device of FIG. 1a

FIG. 3d shows the burette of FIG. 3a.

FIG. 4a shows a base unit and a burette adopted for ultrasound measurements of the urine level in the burette. The figure includes two cross sectional views.

FIG. 4b shows a further cross sectional view to show ultrasound propagation of the base unit and burette of FIG. 4a.

DETAILED DESCRIPTION

FIGS. 1a to 1f shows a urine measuring device 100 for measuring of urine production of a patient carrying a urine catheter, the device comprising a measurement vessel, or chamber 120, also called burette, provided with a siphon for self emptying when the burette 120 becomes filled up to a predetermined volume. The burette 120 further comprises an inlet 122 and an outlet 130, 160 for the urine whose volume is to be measured. Further, the device comprises a base unit 105 provided with a cavern 138 for placing the burette 120 into, the side walls of the cavern 138 having left 139, right 137 and back 136 side walls, and being provided with two capacitance electrodes 140, 141 placed apart relative to each other, and capable of sensing a capacitance signal occurring between the two capacitance electrodes. The burette 120 is provided with a ventilation opening 106 to allow air to escape the burette when urine enters. The ventilation opening 106 is preferably provided with a hydrophobic filter to prevent urine from accidentally leaving the self-emptying chamber 120. The capacitance signal changes as the level of urine in the burette 120 changes, and the capacitance signal constitutes a measure of the produced amount of urine. A processor 610 is arranged to, with the aid of signal processing of the capacitance signal, keep record of how many times the burette has been emptied, and to continuously monitor the urine volume production between emptyings. The processor is configured to calculate the urine production as a function of time. The processor is preferably arranged in the base unit 105.

The burette 120 may be a disposable article. An advantage of having the burette as a dispose article is that a step of washing and sterilising a complicated structure for use with another patient, or with the same patient at a later stage, is eliminated. The burette does not have to be manufactured in a rugged re-useable material capable of withstanding repeated washing and handling.

The capacitance electrodes 140 are preferably of a length reaching from a position corresponding to a bottom end of the burette and to a position corresponding to an upper end of the burette. The capacitance electrodes may end at a maximum filling level of the burette. Above this level self emptying takes place. The burette suitably empties into a conventional urinary collection bag attachable to the burette outlet 130, 160.

By inventive thinking and by experimentation, the inventor(s) have found that if the electrodes are arranged besides each other, the distance between them should be large in comparison with the thickness of the wall of the burette. Electrodes having a width of 5 to 20 mm should function well. However, the electrodes should be considerably less wide than the burette. This would reduce the risk of picking up disturbances or interference. Electrodes less wide than 5 mm may give a little bit weak signal, even if low signal level seems to appear first when the width becomes less than one mm.

The electrodes may be made wider as the burette widens upwards, such that a capacitance signal becomes linear with the volume, instead of with the height. For reasons of manufacturing technology, the burette may have taper angles. If the burette is manufactured from two halves, it is possible to have constant width inside.

The cavern 138 of the base unit 105 may be an open cavern, i.e., not completely surrounding the walls of the burette 120, enabling the burette including catheters connected to the inlet and the outlet to be placed in the cavern without the need to disconnect one or more of the catheters. The cavern is preferably provided with three walls; a back wall 136, a left side wall 139, and a right side wall 137, the cavern 138 is preferably open, or partly open, upwards and downwards to let inlet and catheter tubing pass from above, and to let outlet pass downwards. The cavern is preferably open at the front to enable visual inspection of the urine level in the burette 120. The left 139 and right 137 side walls may preferably be arranged slightly slanting to confer a narrowing cross section to the cavern in the downwards direction. Correspondingly, the burette may be given a slightly tapering shape to provide a snug and consistent fit of the burette in the cavern. The snug and consistent fit assures good measuring conditions for particularly the capacitance electrodes.

The burette may preferably have a measurement volume of between 10 and 30 milliliter, and even more preferred, a measurement volume of between 14 and 16 milliliter. These volumes have shown to be particularly advantageous as to the time the urine spends in the burette 120. It is an advantage to have fresh urine in the burette. However in a too small burette, capillary forces may interfere with the siphoning function, and/or the filling of the burette. The base unit may be provided with a measuring scale arranged next to the burette for easy check of the electronic measuring function.

The burette 120 may have a quadratic or oval cross section and be provided with two planar side walls to fit snugly toward the capacitance electrodes 140 of the cavern of the base unit 105.

A front wall of the burette 120 may advantageously be made of a transparent polymer to allow for visual inspection of the siphon and the urine level inside. A visual measurement scale may be printed or cast at burette surface for visual measurement of urine level.

Figure 1A:
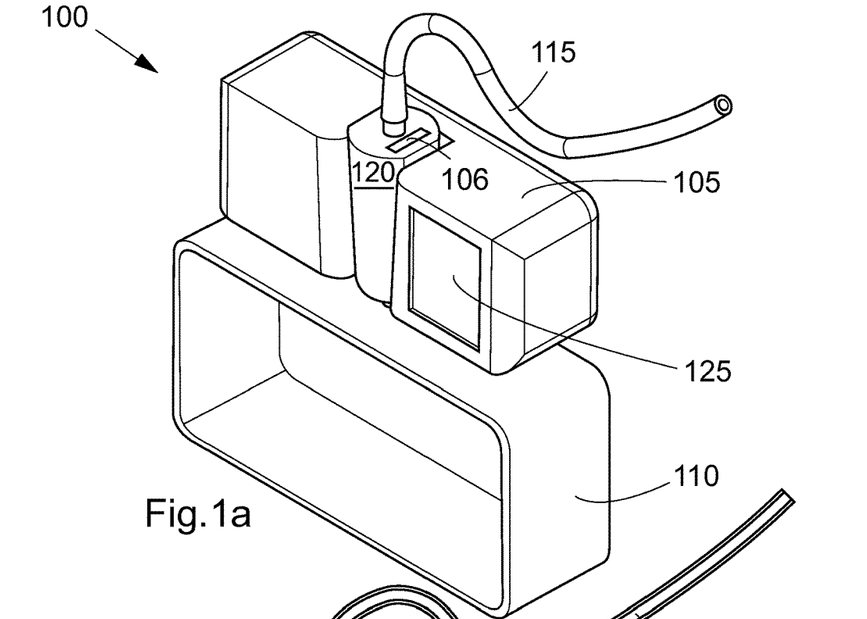
FIG. 1a shows a perspective view of urine measuring device for measuring of urine production.
Figure 1B:
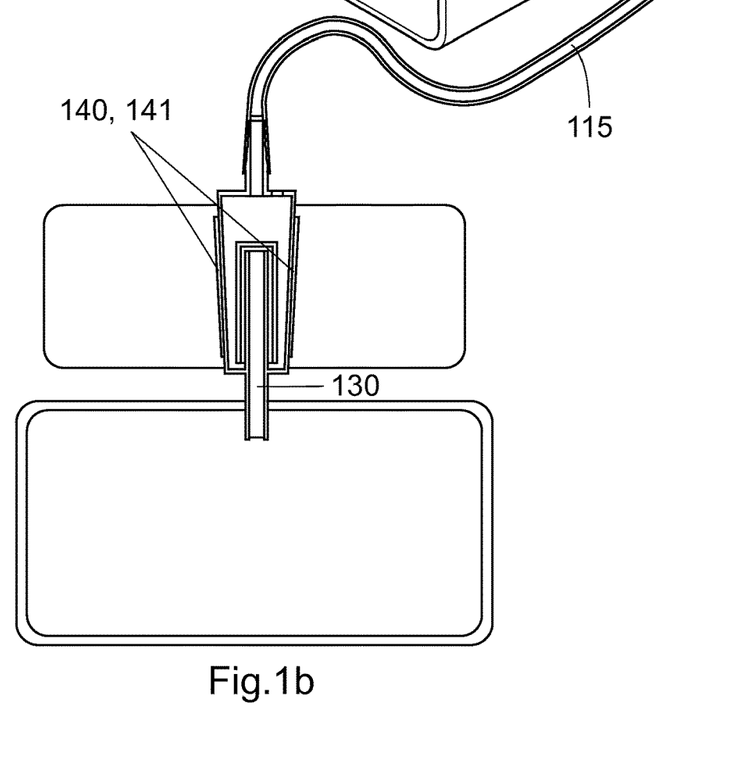
FIG. 1b shows the device of FIG. 1a in a planar cross section.
Figure 1C:
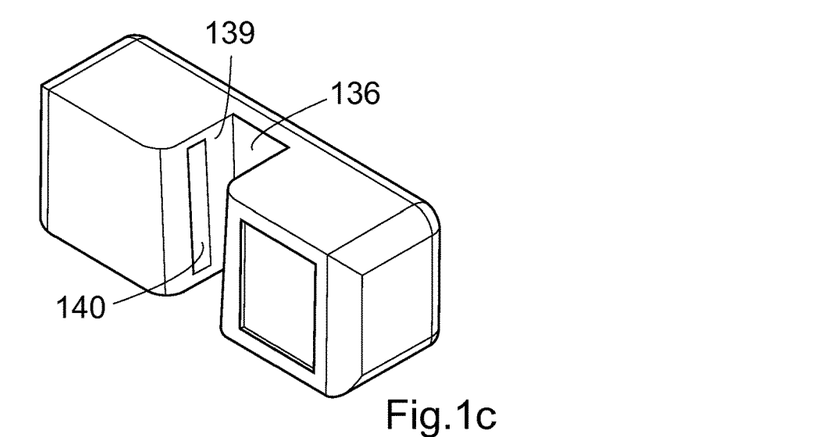
Figure 1D:
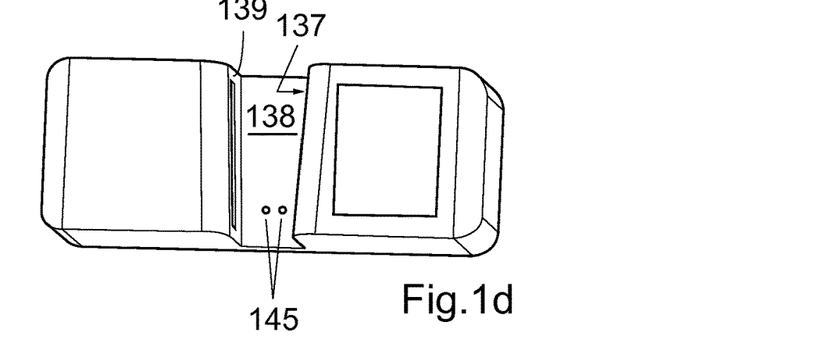
Figure 1E:
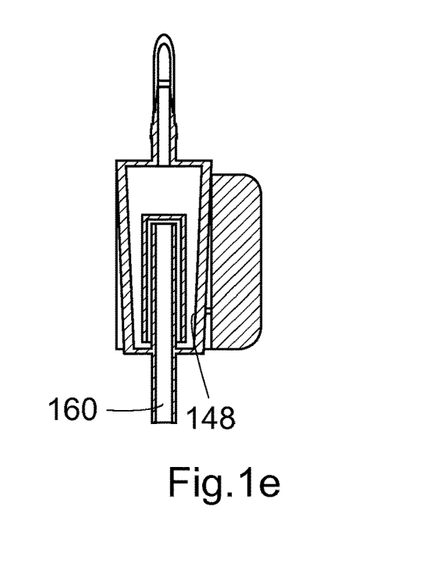
FIG. 1e shows, in cross section, a siphon measurement chamber (burette) placed in a cavern of the base unit.
Figure 1F:
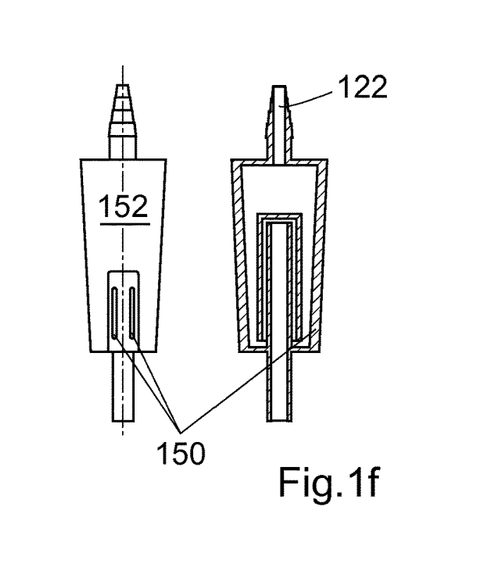
FIG. 1f shows the burette from the behind and in cross section.

There may be arranged two conductance electrodes 148 on the inside of the burette to come into contact with the urine and which conductance electrodes 148 are connected to contact plates 150 arranged on the outside of the burette 120. The contact plates 150 arranged on the outside of the burette 120 may be arranged at a back wall 152 of the burette 120. Further, two connection contacts 145 may be arranged in a back wall 136 of the cavern to make contact to the contact plates 150 of the burette 120 to convey a conductance signal to the base unit for signal processing and measurements.

The device may further be provided with means for combining capacitance and resistance/conductance measurements to improve volume measurements.

The outlet pipe 160 may be of a certain length and may be provided with a cross section area that is gradually increasing towards an outlet end.

Measurement Signal

The processing of signals is aimed to provide a urine production signal as a function of time. The base unit may be provided with a display 125 for displaying the urine production as a function of time. A value representing the production the last hour may be displayed. A value representing the production the last 24 hours may be displayed. A value representing the current volume in the burette may be displayed. A value representing urine volume since last replacement of bag may be displayed.

Figure 2:
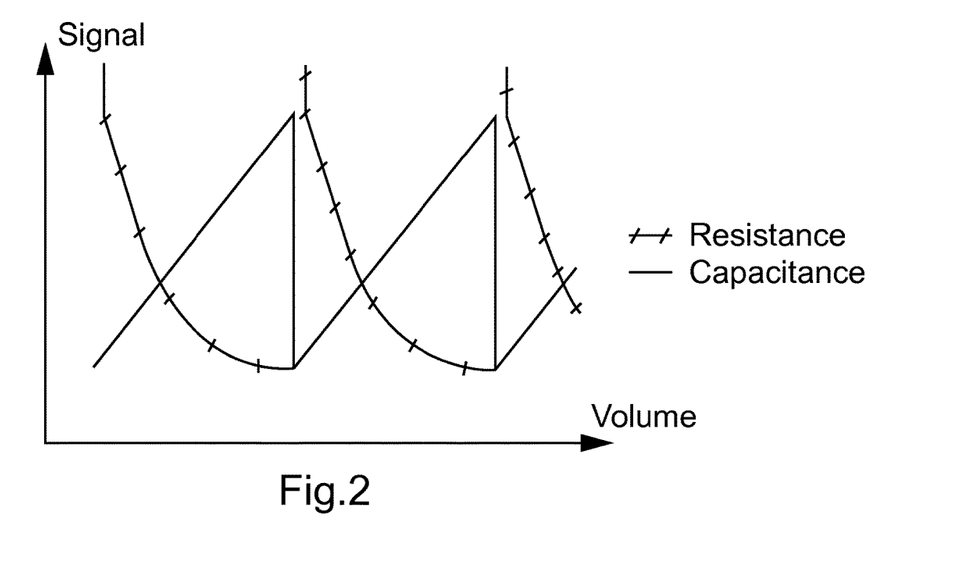
FIG. 2 shows an example diagram of how resistance values and capacitance values depend of produced urine volume.

FIG. 2 shows an example diagram of how resistance values and capacitance values depend of produced urine volume. It can be seen that resistance decreases when volume increases. It can also be seen that capacitance increases proportionally with increasing volume.

The volume in the burette may be determined as follows:

$$V(t)=K1(C(t)+K2) \quad \text{(I)}$$

where V(t) is the volume, C(t) is the capacitance signal, R(t) is the resistance signal, K1 and K2 are constants.

The constants may be recalculated after each emptying to make up for possible drift in the system.

As an alternative, using also resistance measurements $$V(t)=K1(C(t)+K2)+K3/(K4+R(t))+K5 \quad \text{(II)}$$

where V(t) is the volume, C(t) is the capacitance signal, R(t) is the resistance signal, and K1-K5 are constants.

As a further alternative the influence of the two portions of the equation (II) are given different importance, i.e., in the beginning of the filling of the burette the resistance portion dominates, and subsequently diminishes. If starting with equations (III) and (IV) below, the volume can be determined as will be explained further below.

$$V\_c(t)=K1(C(t)+K2) \quad \text{(III)}$$

$$V\_r(t)=K3/(K4+R(t))+K5 \quad \text{(IV)}$$

Here, V_c(t) is the volume in the burette calculated from resistance measurements only, and V_r(t) is the volume in the burette calculated from capacitance measurements only.

Now, if V_r(t) is less than a certain resistance value R_limit then the volume in the burette is determined as V(t)=V_r(t), i.e., as from equation (IV)

Else if V_c(t) is greater than a certain capacitance value C_limit then the volume in the burette is determined as V(t)=V_c(t), i.e., as from equation (III). In all other cases the volume is determined as a weighted sum; a first ratio between the current volume calculated from capacitance measurement only, and maximum volume, is calculated. A second ratio is calculated as the difference between 1.00 and the first ratio. The volume is then calculated as a sum of a first and a second product. The first product is the volume based on capacitance measurements only weighted by the second ratio. The second product is the volume based on resistance measurements only weighted by the first ratio. See the expressions V, VII, VII below.

$$R\_ratio=V\_c(t)/V\_max \quad \text{(V)}$$

$$C\_ratio=1-R\_ratio \quad \text{(VII)}$$

$$V(t)=C\_ratio\ V\_c(t)+R\_ratio\ V\_r(t) \quad \text{(VIII)}$$

The volume may also be determined by feeding capacitance and resistance values to a Kalman filter.

Capacitance measurements are shown above to be accomplished with the aid of two capacitance electrodes. As an alternative, capacitance measurements may be accomplished with the aid of four capacitance electrodes.

Impedance/Conductivity Determination

The display may also display an impedance/resistance value, or a corresponding conductivity value reflecting an electrolyte concentration in the urine. The impedance measurements may take into account the calculated volume of urine at the point in time when the impedance measurement is made. In the calculations it may be taken into account the estimated volume to get even more accurate impedance determinations. Additionally, or as an alternative, measurements may be done at a point in time where most accurate readings are expected, usually when the burette is close to full.

Figure 3A:
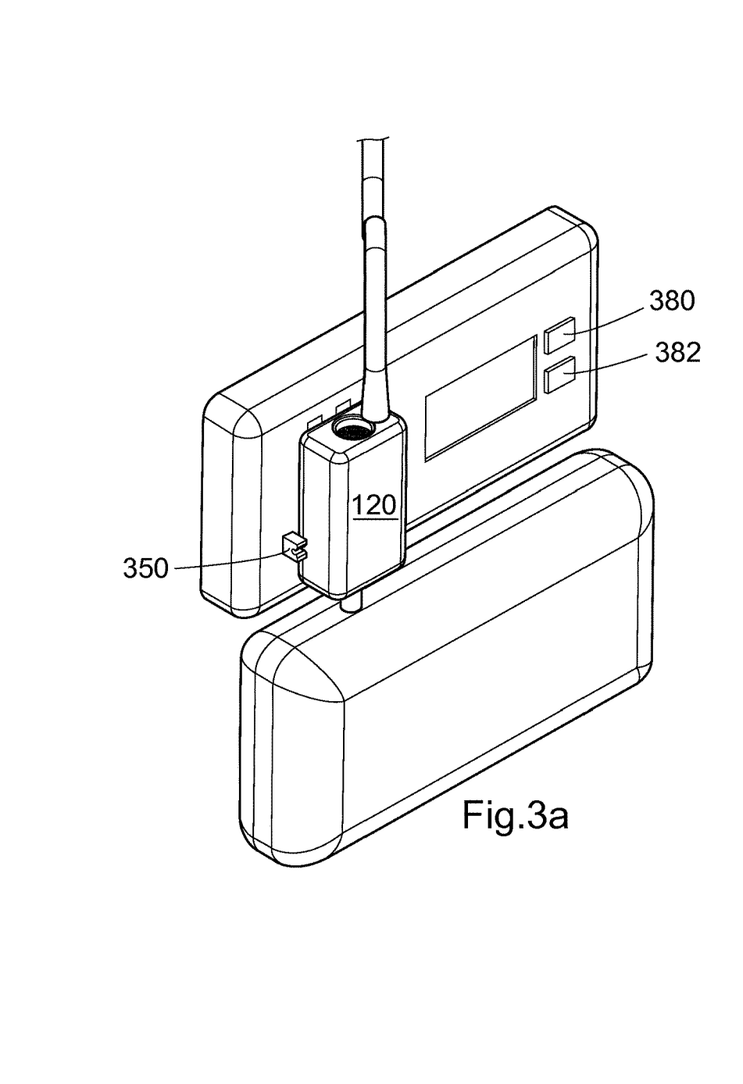
FIG. 3a shows a urine measuring device wherein a burette is attached to a base unit having capacitance electrodes arranged on a flat surface.

FIG. 3a shows a urine measuring device wherein the burette 120 is attached to a base unit 105 having capacitance electrodes 310, 320 arranged at a flat surface 330. There is also provided attachment means 350, 351 to attach the burette 120 removably to the base unit 105. The attachment means comprises two click holders 350 fixed to the base unit 105, and two pins 351 to cooperate with the click holders 350 to keep the burette in place. The two pins 351 may be manufactured of an electrically conducting material, and arranged to pass the burette wall to make electrical contact with the urine in the burette 120, to enable for the electrical measurements. The portion of the each pin extending outside the burette are arranged to make electrical contact to the corresponding click holder 350 to enable electrical measurements of urine conductivity to be made, by sending a current through the urine via one click holder and pin and collecting it at the other pin and click holder. The click holders 350 may be designed of a polymer material and having inlays or contact plates arranged at contact surfaces. It is an advantage to let the pins 351 and click holders function as both mechanical attachment means and electrical contact means as this saves material and complexity and thus manufacturing costs. The burette is simply put into place by pressing the burette with the pins into place and it snaps easily into place as each click holder has two arms 352, 353 partially embracing a cylindrical space corresponding to the shape of the pin.

Figure 3B:
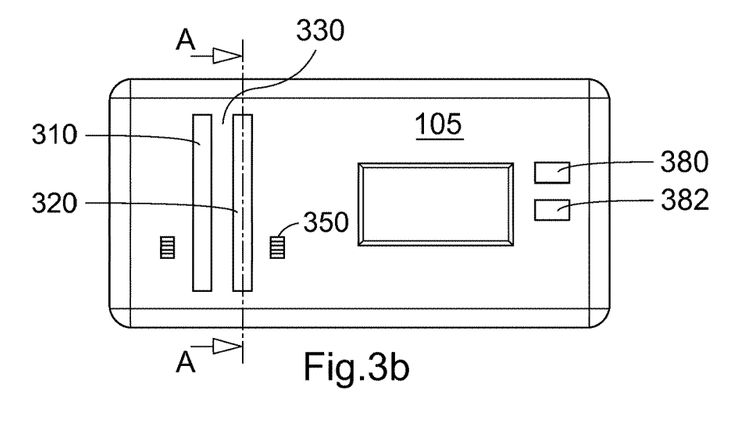
FIG. 3b shows a base unit of the device of FIG. 3a, with the burette removed.

FIG. 3b shows a base unit 105 of the device of FIG. 3a, with the burette 120 removed. Two electrodes 310, 320 are arranged on the surface 330 extending in a vertical direction, to enable capacitance measurements as the capacitance changes due to changes in urine level in the burette 120.

Figure 3C:
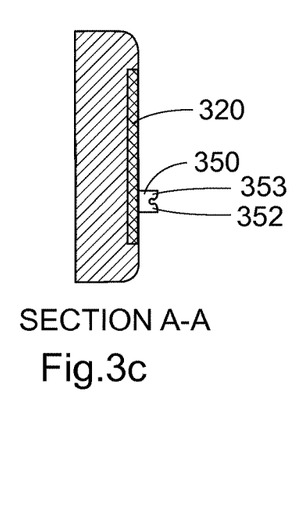
FIG. 3c shows the base unit of FIG. 3b in cross section.

FIG. 3c shows the base unit 105 of FIG. 3b in cross section. Here, one of the capacitance electrodes 320 and click holders 350 can be seen in more detail.

Figure 3D:
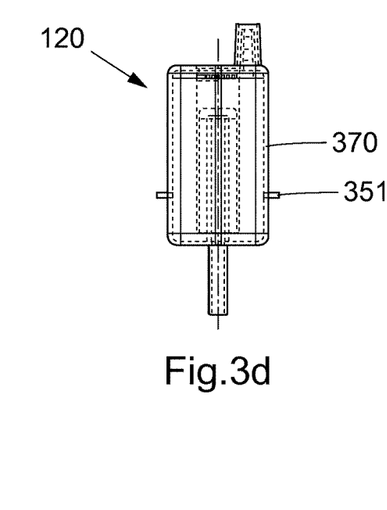

FIG. 3d shows the burette in a see-through view. It can be seen that the pin 351 is attached in the wall 370 of the burette 120, and also extends through the wall 370.

Ultrasound Measurement

Figures 4A, 4B:
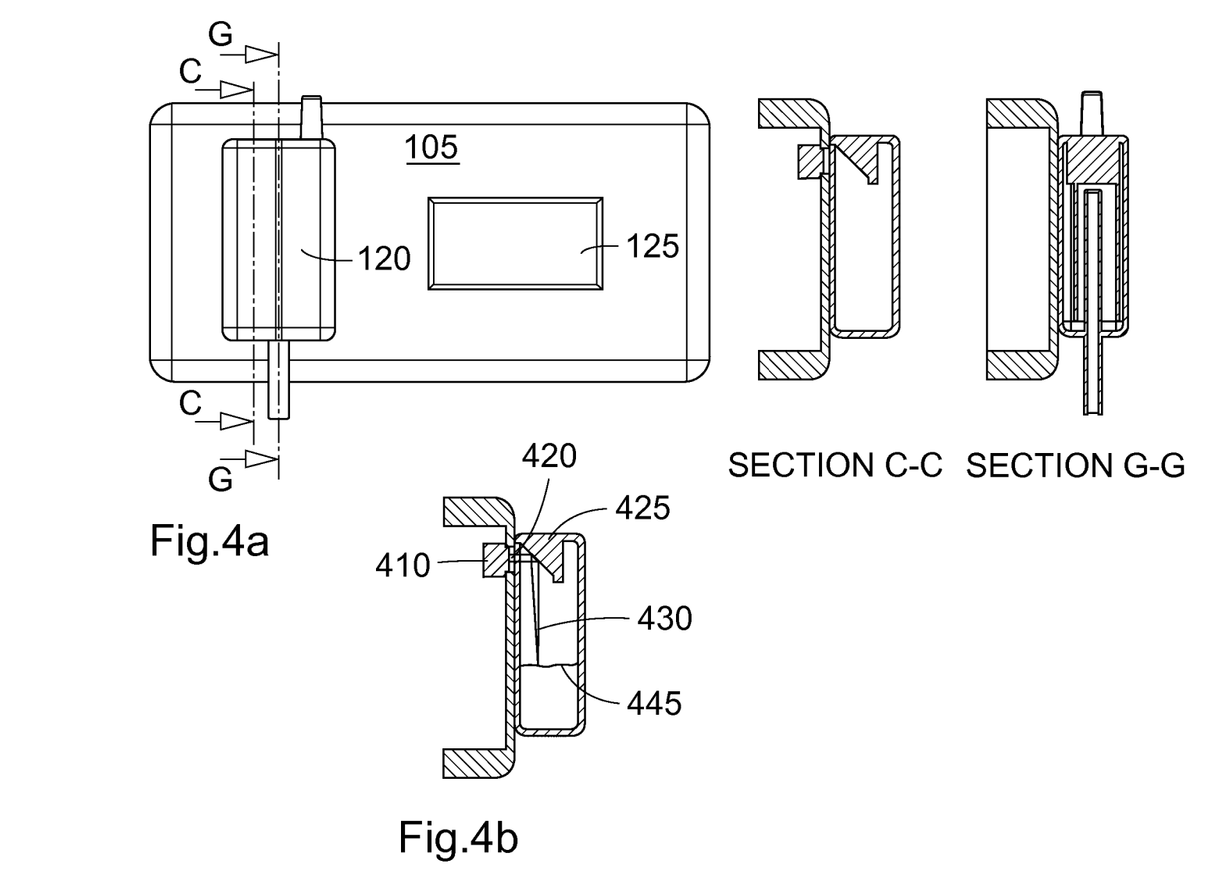
Figure 4C:
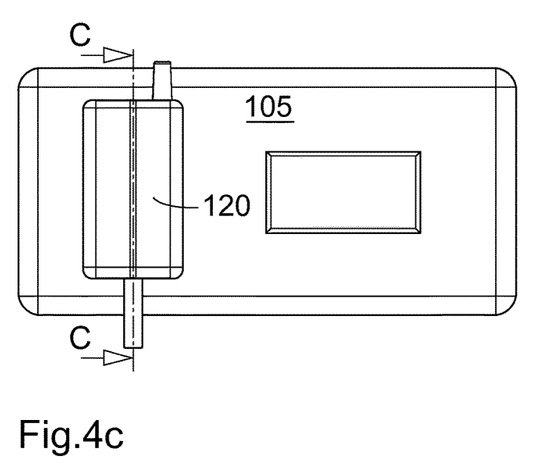
FIGS. 4c to 4g shows a base unit and a burette wherein the level of urine is measured using a pressure sensing system.
Figure 4D:
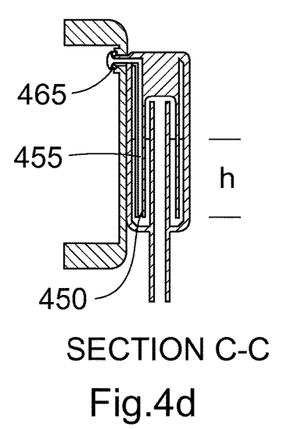
Figure 4E:
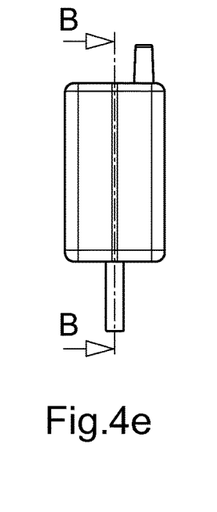
Figure 4F:
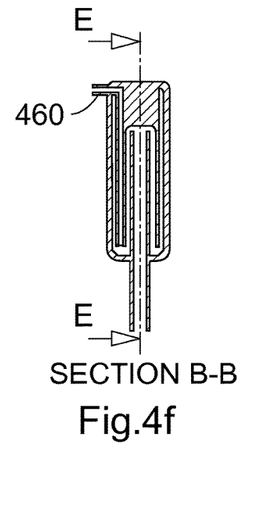
Figure 4G:
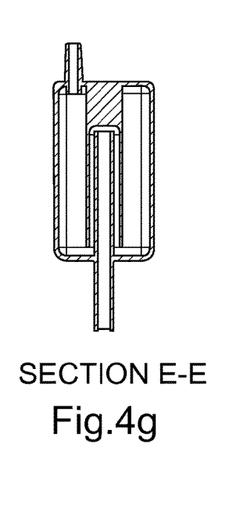

FIG. 4a shows a base unit 105 and a burette 120 adopted for ultrasound measurements of the urine level in the burette 120. The figure includes two cross sectional views.

FIG. 4b shows a further cross sectional view to show ultrasound propagation of the base unit 105 and burette 120 of FIG. 4a. The base unit 105 and burette may thus be provided with an ultrasound measurement system as a complement, or as an alternative, to the capacitive measurement system as described above. The base unit 105 may be provided with an ultrasound transceiver 410, a hydrophobic filter 420, and an ultrasound beam reflector 425. The ultrasound transceiver 410 is preferably arranged at an upper portion of the base unit 105 such that an ultrasound beam can be made crossing a hydrophobic filter window of the burette to enter the burette. Further the burette may be provided with an ultrasound beam reflector 425 for deflecting the ultrasound beam towards the urine surface. Urine level can be determined by measuring the time needed for an ultrasound pulse to travel to the urine surface 445 and back, and using knowledge of the dimensions of the burette, and the location and dimensions of the ultrasound beam reflector 425.

Pressure Measurement

FIGS. 4c to 4g shows a base unit 105 and a burette 120 wherein the level of urine is measured using a pressure sensing system. This can be used as an alternative or as a complement to the other measurement methods. The burette is provided with means to allow attachment to the base unit 105. Preferably, the burette can be attached to the base unit with the aid of a pipe end 460 insertable to a socket in the base unit 105. The socket being provided with pressure tight sealing means 465, e.g. an O-ring to let pressure from an ascending pipe 455 travel to a pressure meter (not shown) of the base unit 105. The ascending pipe extending from a bottom end 450 near the bottom of the burette and upwards, covering the entire length of the siphon of the burette. In this way, pressure build up due to increasing level of urine in the burette is transferred via the ascending pipe and the ascending pipe end 460 to the base unit. It is an advantage that the pipe end 460 is used to solve two problems at the same time; first; to attach burette 120 to base unit 105 and second; to transfer pressure from ascending pipe to pressure meter of base unit 105. The pipe end 460, or the inlet opening for the pipe end 460 may preferably be provided with a hydrophobic filter to prevent urine from accidentally entering the base unit.

Figure 5A:
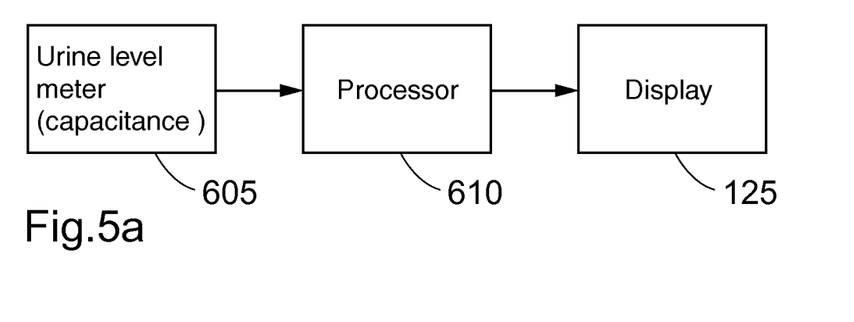
FIGS. 5a, 5b, and 5c shows block diagrams of some urine measurement systems of different compositions.
Figure 5B:
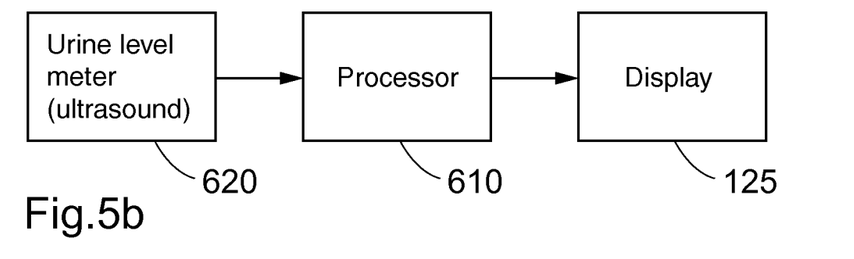
Figure 5C:
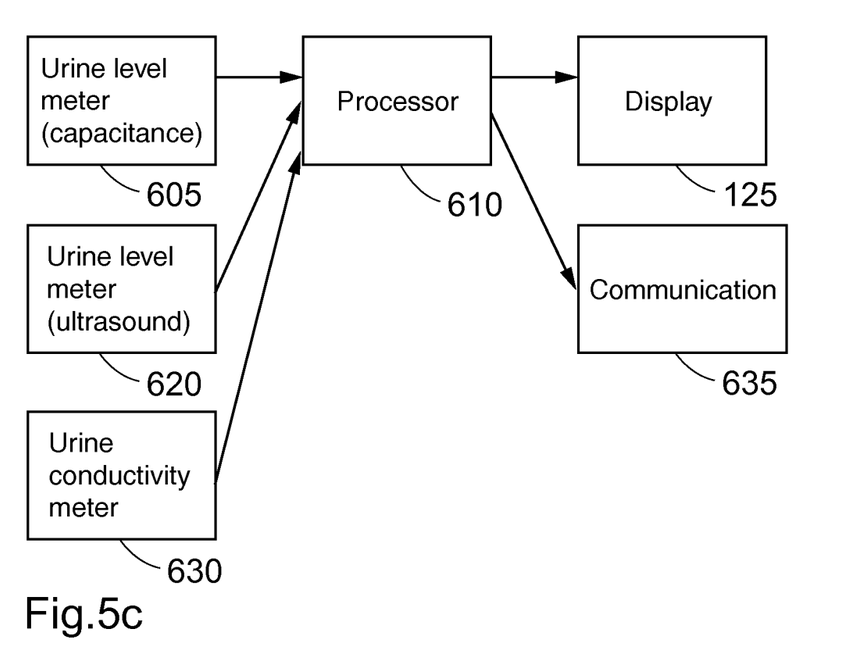

FIGS. 5a, 5b, and 5c shows block diagrams of some urine measurement systems of different compositions. A urine measurement system may comprise a capacitive urine level meter 605, or an ultrasound urine level meter 620, or a pressure meter, or two or more thereof. The urine measurement system comprises a processor unit 610, and a display 125 or a communications unit 635, or both and with suitable connections with each other and with the meters mentioned above. The system may also comprise a urine conductivity meter 630.

Input Organ and Event Marker

The device may also be provided with an event marker. The event marker comprises an input organ, e.g. one or more buttons 380, for entering that an event that may influence the urine production of the patient has occurred. The event marker also comprises electronics and/or software arranged to mark the event with a symbol in a graphics presentation of the urine production as a function of time. Thus, the event marker constitutes a time stamp to be shown in a graphics layout, either in the display 125 or at a remote patient monitor, or in a printout, or in a combination of those. There may be arranged for marking two or more types of events, such as administering diuretics, change of infusion bag, change of infusion velocity, etc. In this way the nursing personnel are given the possibility to see in a clear and concise manner from the curve and the timeline position of the event marker graphics symbols if the desired effect of a measure was achieved within an estimated time. Event marker graphics symbols may e.g. be one or more arrows, markers, or stars, or a combination of those.

The device may also be provided with a suitable input organ 382 for zeroing and/or resetting.

Method

Figure 6:
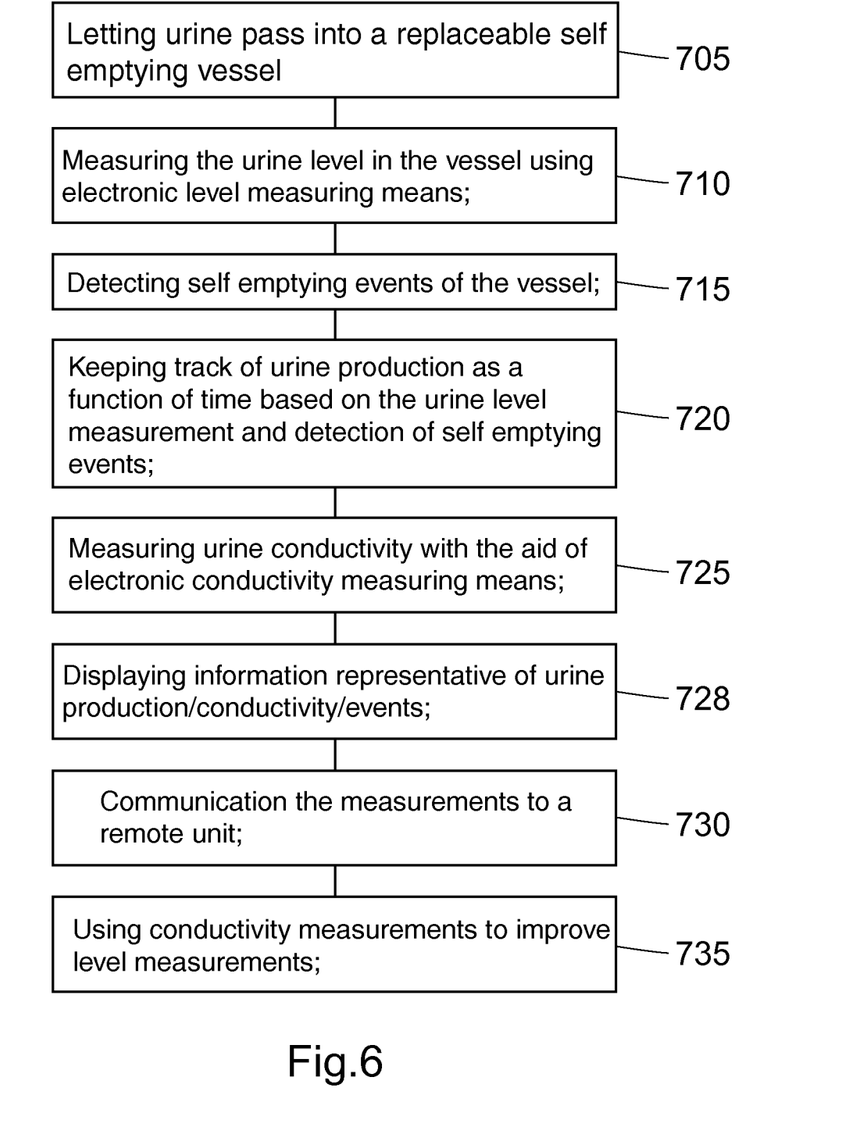
FIG. 6 shows a flow chart of a method for precise measuring of urine production of a patient.

FIG. 6 shows a flow chart of a method for precise measuring of urine production of a patient. The method comprises the following steps:
  letting (705) urine pass from the patient into a self emptying vessel;
  measuring (710) continuously the urine level in the vessel using electronic level measuring means arranged apart from the burette;
  detecting (715) self emptying events of the vessel;
  keeping (720) track of urine production as a function of time based on the urine level measurement and detection of self emptying events;

Additionally, in the method, the self emptying vessel is a replaceable self emptying vessel. Preferably the self emptying vessel is a burette. Even more preferred the burette is a burette with a siphoning system for self emptying. Preferably the urine emptied from the vessel is emptied into a conventional collection bag.

The electronic measuring means may be capacitive, ultrasound or pressure as described above.

The method may further comprise the step of:
  measuring (725) urine conductivity with the aid of electronic conductivity measuring means;
  and/or
  communicating (730) the measurements to a remote unit;
  and/or
  using (735) conductivity measurements to improve level measurements;
wherein the method to improve may be the one as described above.

The invention claimed is:

1. A urine measuring device for measuring urine production of a patient carrying a urine catheter, comprising:
  a self-emptying siphon, which comprises an inlet connectable to the catheter and an outlet for the urine whose volume is to be measured; and a base unit comprising:
  an attachment organ configured to removably attach the self-emptying siphon to the base unit, and
  a urine level measurement organ, configured to sense changes in a level of urine in the self-emptying siphon, and wherein the urine level measurement organ comprises two planar capacitance electrodes placed apart relative to each other on the base unit, a capacitance signal occurring between the two planar capacitance electrodes; and wherein the planar capacitance electrodes are positioned on the base unit in respective locations of the base unit relative to the attachment organ and over vertical distances where, when the self-emptying siphon is held to the base unit with the attachment organ, each of the planar capacitance electrodes extends at least from a position outside of the siphon in the base unit directly radially outwards of a bottom end of the siphon to a position outside of the siphon in the base unit directly radially outwards of an upper end of the siphon, the capacitance signal occurring between the two planar capacitance electrodes continuously changes as the level of urine in the self-emptying siphon changes, the capacitance signal therefore constitutes a continuous measure of the produced amount of urine, wherein the base unit further comprises a processor that is configured to keep record of how many times the self-emptying siphon has been emptied, and thus calculates the urine production as a function of time.

2. The device according to claim 1, wherein the processor is configured to calculate the volume of urine produced based on a urine level signal measured by the urine level measurement organ.

3. The device according to claim 1, wherein the processor is arranged to calculate the volume of urine in the self-emptying siphon, and also arranged to keep record of how many times the self-emptying siphon has been emptied, and thus is arranged to calculate the urine production as a function of time based on the capacitance signal.

4. The device according to claim 1, wherein the attachment organ is an open cavern.

5. The device according to claim 4, wherein the cavern is defined by a first limiting wall, a second limiting wall, and a third limiting wall.

6. The device according to claim 1, wherein the urine level measurement organ further comprises an ultrasound meter system configured to determine the level of urine in the self-emptying siphon.

7. The device according to claim 6, wherein the ultrasound meter system comprises an ultrasound transducer arranged at the base unit and configured to emit and receive ultrasound.

8. The device according to claim 7, wherein the self-emptying siphon comprises an ultrasound beam reflector configured to direct an ultrasound beam towards a urine fluid surface.

9. The device according to claim 6, wherein the self-emptying siphon comprises a hydrophobic filter arranged to let an ultrasound beam pass from the ultrasound transducer through an opening in the wall of the self-emptying siphon having the hydrophobic filter, and into an interior of the self-emptying siphon.

10. The device according to claim 1, wherein the urine level measurement organ further comprises a pressure metering system configured to determine the level of urine in the self-emptying siphon.

11. The device according to claim 10, wherein the pressure metering system comprises an ascending pipe having organs removably connectable to a pressure sensor of the base unit.

12. The device according to claim 1, wherein the self-emptying siphon has a quadratic or oval cross section and comprises at least one planar wall that engages the capacitance electrodes.

13. The device according to claim 1, wherein one or more external walls of the self-emptying siphon contact the capacitance electrodes, the one or more external walls are made of polymer.

14. The device according to claim 1, wherein the self-emptying siphon comprises two conductance electrodes arranged on the inside of the self-emptying siphon to come into contact with the urine and are connected to contact plates arranged on the outside of the self-emptying siphon.

15. The device according to claim 14, wherein the contact plates arranged on the outside of the self-emptying siphon are arranged at a back wall of the self-emptying siphon.

16. The device according to claim 14, wherein the base unit further comprises two connection contacts arranged to make contact to the contact plates of the self-emptying siphon to acquire a conductance signal for signal processing and measurements.

17. The device according to claim 14, wherein the processor is arranged to calculate the volume of urine produced based on capacitance measurements and conductance measurements in combination.

18. The device according to claim 6, wherein the processor is arranged to calculate the volume of urine produced based on capacitance and ultrasound measurements in combination.

19. The device according to claim 18, further comprising a urine conductivity meter and wherein the processor is arranged to calculate the volume of urine produced based on capacitance, ultrasound, and conductivity measurements in combination.

20. The device according to claim 1, wherein an outlet pipe is provided with a cross section area that is gradually increasing towards an outlet end of the outlet pipe.

21. The device according to claim 1, wherein the base unit is provided with an input organ for marking events.

22. The device according to claim 1, wherein the electrodes extend from the bottom end of the self-emptying siphon to at least a maximum filling level of the self-emptying siphon.

23. A method for monitoring urine production of a patient comprising:
coupling a self-emptying vessel to a base unit;
letting urine pass into a replaceable self-emptying vessel;
measuring continuously, using a processor, a urine level in the vessel using two capacitance electrodes arranged apart from the self-emptying vessel, the two capacitance electrodes being part of the base unit, substantially planar and positioned on the base unit relative to the self-emptying vessel over vertical distances where each of the capacitance electrodes extends at least from a position outside of the siphon directly radially outwards of a bottom end of the siphon to a position outside of the siphon directly radially outwards of an upper end of the siphon and a capacitive signal occurring between the two capacitance electrodes changes as the urine level in the self-emptying vessel changes;
detecting, by operation of the two capacitance electrodes, self-emptying events of the self-emptying vessel from the capacitance signal;
keeping track, by the processor, of the urine production as a function of time based on the urine level measurement and detection of self-emptying events.

24. A urine measuring device for measuring urine production of a patient carrying a urine catheter, comprising:
- a self-emptying siphon, which comprises an inlet connectable to the catheter and an outlet for the urine whose volume is to be measured; and a base unit comprising:
- an attachment organ configured to removably attach the self-emptying siphon to the base unit, and
- a urine level measurement organ, configured to sense changes in a level of urine in the self-emptying siphon, and wherein the urine level measurement organ comprises two capacitance electrodes placed apart relative to each other on the base unit, a capacitance signal occurring between the two capacitance electrodes; and
- wherein the capacitance electrodes are positioned on the base unit in respective locations of the base unit relative to the attachment organ and over vertical distances wherein, when the self-emptying siphon is held to the base unit with the attachment organ, each of the capacitance electrodes extends on the base unit at least from a location of the base unit directly radially outwards of a bottom end of the siphon to a location of the base unit directly radially outwards of an upper end of the siphon, the capacitance signal occurring between the two capacitance electrodes continuously changes as the level of urine in the self-emptying siphon changes, the capacitance signal therefore constitutes a continuous measure of the produced amount of urine, wherein the base unit further comprises a processor that is configured to keep record of how many times the self-emptying siphon has been emptied, and thus calculates the urine production as a function of time.

25. The urine measuring device of claim 24, wherein the capacitance electrodes are substantially flat.

26. The urine measuring device of claim 24, wherein the capacitance electrodes are non-cylindrical.

27. The urine measuring device of claim 24, wherein each of the capacitance electrodes is disposed on an outer surface of the base unit.

\* \* \* \* \*